United States Patent [19]

Saunders

[11] Patent Number: 4,751,001
[45] Date of Patent: Jun. 14, 1988

[54] BLOOD PARTITIONING APPARATUS

[75] Inventor: Alex M. Saunders, San Carlos, Calif.

[73] Assignee: Becton Dickinson and Company, Franklin Lakes, N.J.

[21] Appl. No.: 653,178

[22] Filed: Sep. 24, 1984

[51] Int. Cl.$^4$ .............................................. B01D 21/26
[52] U.S. Cl. .................... 210/516; 422/101; 436/177
[58] Field of Search ............ 422/101; 436/177; 494/16–20; 210/516, 518, 927, 514; 435/2

[56] References Cited

U.S. PATENT DOCUMENTS

| 3,852,194 | 12/1974 | Zine, Jr. ................... 494/38 X |
|---|---|---|
| 4,101,422 | 7/1978 | Lamont et al. ............. 210/927 X |
| 4,147,628 | 4/1979 | Bennett et al. ............ 210/518 X |
| 4,153,739 | 5/1979 | Kessler ....................... 427/2 |
| 4,190,535 | 2/1980 | Luderer ...................... 210/789 |
| 4,255,256 | 3/1981 | Ferrante et al. ........... 210/927 X |
| 4,310,430 | 1/1982 | Ichikawa .................... 210/927 X |
| 4,350,593 | 9/1982 | Kessler ...................... 210/927 X |
| 4,457,782 | 7/1984 | Honda et al. .............. 210/516 X |
| 4,487,700 | 12/1984 | Kanter ........................ 210/789 |
| 4,534,798 | 8/1985 | Honda et al. .............. 210/927 X |

FOREIGN PATENT DOCUMENTS 2014879A 2/1979 United Kingdom .

OTHER PUBLICATIONS

Chemical Abstract 9265X–Scand. J. Clin. Lab. Invest.

Primary Examiner—Richard V. Fisher
Assistant Examiner—W. Gary Jones
Attorney, Agent, or Firm—Hoffman & Baron

[57] ABSTRACT

The present invention is directed to a method for separating mononuclear cells from other cells in a blood sample which is more rapid than the currently used density gradient material and which provides a better separation than methods utilizing thixotropic, gel-like material. In the method, a water soluble density gradient material is placed in a centrifuged tube. A water insoluble, thixotropic, gel-like substance is also placed in the container. A blood sample is placed in the container and the container is centrifuged for a time during which various components interchange positions and the gel-like substance forms a barrier between the mononuclear cells and the other cells of the blood sample.

16 Claims, 1 Drawing Sheet

BLOOD PARTITIONING APPARATUS

BACKGROUND OF THE INVENTION

1. Field of the Invention

The present invention relates generally to a method and apparatus for partitioning a heavier phase from a lighter phase of a centrifugally separated multiphase fluid specimen. More particularly, the present invention is directed to a method and apparatus for separating platelets, lymphocytes and monocytes from granulocytes and erythrocytes in a blood specimen.

2. Description of the Prior Art

The Immunological analysis of blood generally requires the isolation and separation of the lymphocytes for detailed analysis. In general, two distinct methods are known for the separation of lymphocytes from other blood cells. The first of these methods involves buoyant density centrifugation of cells through a particular newtonian fluid. The most commonly used fluid is known as Ficoll-Paque TM, a water soluble liquid having a specific gravity of 1.077 g/cc, which is marketed by Pharmacia Fine Chemicals AB, Upsala, Sweden. The second of these methods utilizes a non-newtonian, water-insoluble, thixotropic, gel-like substance which establishes a continuous semi-rigid gel-like seal across the interior of a container between the lighter phase containing the lymphocytes and a heavier phase containing the erythrocytes and granulocytes.

The Ficoll-Paque TM method contemplates the following general steps:

(1) A predetermined amount of Ficoll-Paque TM is dispensed into the bottom of a container suitable for centrifugation, such as a test tube;

(2) A sample of whole or diluted blood is carefully pipetted onto the surface of the Ficoll-Paque TM;

(3) The Ficoll-Paque TM/blood preparation is then centrifuged at about 400 g for about 30 minutes to provide a layered separation of blood constituents into a top lighter phase containing a mononuclear cell layer including the lymphocytes and a bottom heavier phase containing the erythrocytes and granulocytes which pass into and/or through the Ficoll-Paque TM;

(4) An upper plasma layer is removed by pipetting, leaving behind a lymphocyte layer on the surface of the Ficoll-Paque TM.

(5) A clean Pasteur pipette is used to transfer the lymphocyte layer to a clean centrifuge tube.

The Ficoll-Paque TM method has several disadvantages. First, very careful technique by the operator of the Ficoll-Paque TM method is required. If the initial introduction of the blood sample is performed carelessly, plasma may be deployed below the surface of the Ficoll-Paque TM medium causing reduced local specific gravity of the Ficoll-Paque TM which is then inadequate to separate lymphocytes and monocytes from other cells.

Second, careful technique is again required to transfer the lymphocyte layer from the surface of the Ficoll-Paque TM to a clean centrifuge tube for washing. It is critical to remove all the interface but a minimum amount of Ficoll-Paque TM during this transfer step.

Third, centrifugation forces higher than about 400 g cannot be utilized since the Ficoll-Paque TM is water soluble and higher centrifugation forces dilution of the Ficoll-Paque TM with the blood plasma, thereby resulting in a change in the Ficoll-Paque TM specific gravity and a substantial alteration in the separation efficiency.

Fourth, if during centrifugation lighter phases in the blood are carried into the Ficoll-Paque TM medium, they cannot thereafter ascend through the medium. This is due to the low forces produced by the required centrifugation forces of about 400 g.

Fifth, the method requires 1 to 2 hours for completion. A more rapid process would be highly desirable.

A more rapid process is provided by methods which utilize a non-newtonian water immiscible, thixotropic, gel-like substance (hereinafter referred to as a "gel-like substance") for establishing a barrier between the lighter phase containing the lymphocytes and a heavier phase containing the erythrocytes and granulocytes. This method is exemplified by U.S. Pat. No. 4,190,535 to Luderer; U.S. Pat. No. 3,852,194 to Zine; U.S. Pat. No. 4,147,628 to Bennett; U.S. Pat. No. 4,350,593 to Kessler; and U.S. Pat. No. 4,153,739 to Kessler. The use of a gel-like substance to establish a barrier layer between the lighter phase and the heavier phase generally provides a more rapid and easier method for separating the lighter phase and heavier phase than the Ficoll-Paque TM method. However, the use of the gel-like substance in a blood separation scheme also has disadvantages. The most important disadvantage is that the the lymphocyte layer which lies immediately above the gel-like substance after the centrifugation step tends to become contaminated with granulocytes which lie immediately below the gel-like substance. It would be desirable to provide a method and apparatus for separating a blood sample into a lighter phase containing lymphocytes and monocytes and a heavier phase containing erythrocytes and granulocytes which is rapid and which provides a distinct uncontaminated sample of lymphocytes for further analysis.

SUMMARY OF THE INVENTION

The present invention is directed to a method for separating lymphocytes and monocytes from erythrocytes and granulocytes in a blood sample which is more rapid than the Ficoll-Paque TM method and which provides a better separation than the methods utilizing a thixotropic gel-like material.

In its broadest terms, the method of the present invention contemplates the following general steps:

(1) A water soluble density gradient material, such as Ficoll-Paque TM, is placed in an open ended container suitable for centrifugation.

(2) A water insoluble, gel-like substance, such as the previously discussed non-newtonian water-in-soluble, thixotropic gel-like substance, is also placed in the container.

(3) A blood sample is placed in the container and the container is centrifuged at a centrifugal force somewhat higher than is used in the Ficoll-Paque TM method, during which time various components interchange position and the gel-like substance forms a barrier between the heavier and lighter blood cells; and (4) The plasma fraction of the blood is removed from above the barrier layer to leave a layer containing the lymphocytes, monocytes and platelets which is easily recovered for further analysis. During the separation process the heavier fraction of the blood containing the erythrocytes and granulocytes pass through the barrier layer, and also through the density gradient material and are restrained in the bottom of the container.

An important feature of the present invention is that, as the heavier cells of the blood pass through the water soluble density gradient material, they carry with them some plasma from the blood. This dilutes a portion of the water soluble density gradient material which then passes during centrifugation through or around the gel-like substance to form an intermediate water soluble density gradient layer above the gel-like substance and beneath the mononuclear cells. This intermediate layer of water soluble density gradient material is effective, in combination with the substantial mass of the water soluble density gradient material lying beneath the layer of gel-like substance to effectively isolate the granulocytes from contamination of the mononuclear layer of cells. This provides a cleaner, more effective separation of the mononuclear cells without being contaminated with granulocytes. The thin layer of water soluble density gradient material provides a cushion support for the mononuclear cell layer during centrifugation which prevents tight packing of the layer of mononuclear cells.

DETAILED DESCRIPTION OF THE INVENTION

Figure 3:
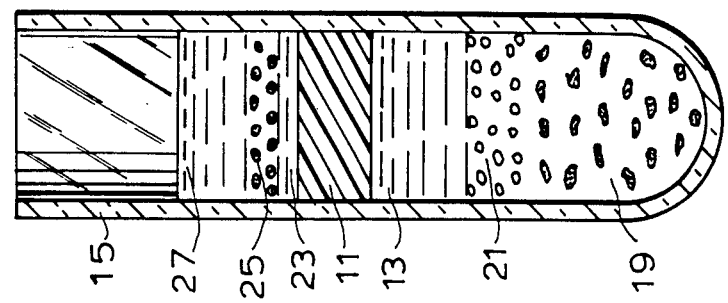
FIG. 3 shows the blood collection tube of FIG. 2 after the sample has been centrifuged.

The formulation or composition of the gel-like substance is not critical. Any of the prior art compositions describing water immiscible, thixotropic, gel-like materials can be used in the method of the present invention. For example, U.S. Pat. No. 4,190,535 describes the use of a mixture of silicone fluid and very fine hydrophobic silica powder to provide a gel-like substance. Also described in this patent is the use of a hydrocarbon gel-like material, polybutane 11-100, marketed by Amoco Chemicals Corporation, Chicago, Ill., and described in that company's bulletin 12-11 as a butylene polymer composed predominantly of high molecular weight mono-olefins (85-98%), the balance being isoparafins. The polybutylene is mixed with fumed silica powder to provide a water-immiscible, thixotropic gel-like material. Also useful is a hydroxyl terminated homopolymer of butadiene with the degree of polymerization being about 50. This is mixed with fumed silica powder to provide a suitable water-immiscible thixotropic, gel-like material. A preferred material for use as the gel-like substance is a polyester, such as that described in U.S. Pat. No. 4,101,422 to Lamont et al. Particularly preferred is a single component polyester #NB 2042-108, a polyester manufactured by Emery Industries, Inc. The polyester composition is particularly preferred for use as the gel-like substance in the present invention since it does not need to be combined with silica powder to provide a suitable specific gravity. It has been determined that the use of silica powder is detrimental to analysis of the recovered lymphocyte fraction in certain apparatus, such as flow cytometry devices. Therefore, the use of a polyester having a suitable specific gravity is preferred.

In general, the gel-like substance should meet the following criteria:

(a) the gel-like substance should have a specific gravity between the specific gravity of the mononuclear cells and the granulocytes and erythrocytes. In general, the specific gravity of the gel-like substance should be from about 1.07 to about 1.085 g/cc, preferably between about 1.075 and about 1.08 g/cc, most preferably 1.077 g/cc;

(b) the gel-like substance should be chemically inert with respect to constituents present in blood;

(c) the gel-like substance is thixotropic. That is, the substance must be capable of flowing under the centrifugal forces used in the separation step to form a barrier following centrifugation but also resists flow and behaves as a highly viscous substance in the absence of high sheer forces.

The water soluble density gradient material is preferably a solution of a polymeric saccharide and a viscosity and density modifying substance. The water-soluble density gradient material is most preferably a Ficoll-Paque TM type of material. Ficoll-Paque TM is an aqueous solution of Ficoll-400 TM and diatrizoate sodium. Ficoll-400 TM is a synthetic high molecular weight ($M_w$ 4000) polymer of sucrose and epichlorohydrin which is easily soluble in water. The molecules of Ficoll-400 TM are highly branched, approximately spherical and have a low intrinsic viscosity compared with linear polysacarides of the same molecular weight. Diatrizoate sodium is a convenient compound to use with Ficoll-400 TM since it forms solutions of low viscosity and high density. Diatrizoate sodium, (molecular weight 635.92) is the sodium salt of 3,5-diacetamido 2,4,6-triiodo benzoic acid. The specific gravity of the density gradient material can be adjusted by varying the amounts of diatrizoate sodium contained in the aqueous solution of Ficoll-400 TM. Ficoll-Paque TM contains 5.7 g Ficoll-400 and 9 g diatrizoate sodium in each 100 ml. For use in the present invention it is preferred to adjust the specific gravity of the water soluble density gradient material to within the range of from about 1.08 to about 1.100 g/cc, preferably from about 1.085 to about 1.095, most preferably 1.09 gm/cc.

For use in the present invention an aqueous solution containing from about 5.7 g to about 6.0 g of sucrose polymer and from about 11.0 g to about 12.0 g of diatrizoate sodium is suitable for use as the water soluble density gradient material.

The method of the present invention is useful with both the conventional open blood collection tube and the closed blood collection tube wherein the opening is closed by a septum penetrable by a needle for insertion of a blood sample. In the open collection tube system, the gel-like substance and the water soluble density gradient material are placed into the tube in a suitable amount in no particular order. For example, in a 7 ml test tube a suitable amount of gel-like substance is about 1.2 grams and a suitable amount of the water soluble density gradient material is about 1.0 grams. This will permit the separation of blood samples of up to about 5 ml. To avoid the problem of careful layering of the blood sample incurred in the density gradient method, the blood collection tube containing the gel-like substance and the water soluble density gradient material may be pre-centrifuged prior to the addition of a blood specimen. Pre-centrifugation causes the water soluble density gradient material to migrate to the bottom of the tube and causes the gel-like substance to form a barrier over the top of the water soluble density gradient material. The blood specimen can then be inserted into the blood collection tube without regard to careful technique. Moderate centrifugation forces of from about 50 g to about 1,000 g for a period of from about 5 minutes to about 0.5 minutes, respectively, are suitable for the pre-centrifugation step.

After the sample is placed into the blood collection tube atop the barrier formed by the gel-like substance, the blood collection tube is centrifuged at a suitable force for a suitable time. In general, a centrifugation force of from about 600 g to about 2000 g is used for a time of from about 20 to about 5 minutes, respectively.

Figure 2:
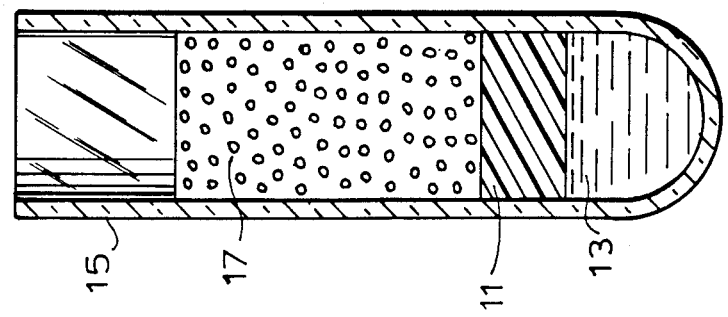
FIG. 2 shows the blood collection tube of FIG. 1 after a blood sample has been placed in the tube prior to centrifugation.
Figure 1:
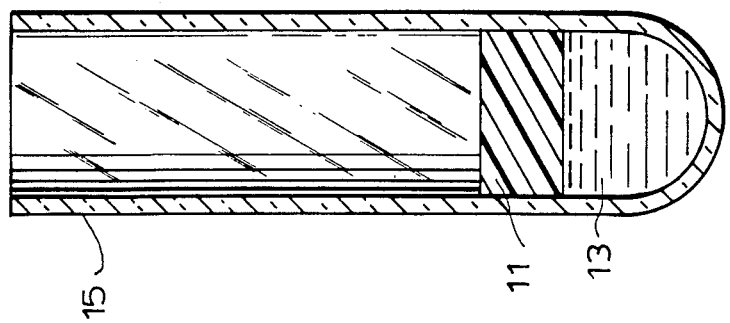
FIG. 1 shows a blood collection tube containing the water immiscible density gradient material and the water soluble density gradient material of the invention.

As shown in FIG. 1, after pre-centrifugation, the gel-like substance 11 forms a barrier atop the water soluble density gradient material 13 in blood collection tube 15. A blood specimen 17 is placed atop the barrier of gel-like substance 11, as shown in FIG. 2. After centrifugation, the blood sample has been caused to separate into several layers, as shown in FIG. 3. The erythrocytes 19 form the bottom most layer. A granulocyte layer 21 lies atop the erythrocytes 19. A major fraction of the water soluble density gradient material lies above the granulocyte layer 21. As previously described, the erythrocytes carry a small part of the blood plasma with them as they migrate through the layer of water soluble density gradient material. This causes some reduction in the specific gravity of a portion of the water soluble density gradient material which migrates during centrifugation past the barrier layer of gel-like substance to form a layer 23 of a minor fraction of water soluble density gradient material as shown in FIG. 3. A layer 25 of lymphocytes, monocytes and platelets lies above the layer 23 of reduced specific gravity water soluble density gradient material 13. The plasma 27 is the topmost layer.

The plasma fraction of the blood is then removed in a manner designed to leave the layer 25 of platelets, lymphocytes and monocytes intact on the surface of the layer 23 of water-soluble density gradient material. The use of a Pasteur pipette is an example of a suitable manner for removing the plasma layer 27, leaving behind an undisturbed layer 25 of lymphocytes, monocytes and platelets. Another example is the use of a syphon tube attached to a vacuum source.

The layer 25 of lymphocytes, monocytes and platelets can then be removed by either of two methods. In one method, a Pasteur pipette is used to transfer the layer 25 to a clean centrifuge tube for washing. In another method, a buffered saline solution can be poured directly onto the top of the layer 25 of mononuclear cells and platelets. The barrier layer 11 of gel-like substance prevents interaction of the buffered saline solution with the granulocytes and erythrocytes. The mononuclear cells can then be removed from atop the barrier layer 11 by simply pouring the mixture of buffered saline solution and mononuclear cells from the collection tube 16.

The following examples further illustrate various features of the invention but are intended to in no way limit the scope of the invention which is set forth in the appended claims.

A sample of whole blood was taken from a single patient. The same blood sample was used for all of the subsequent examples. An aliquot of the blood sample was first used in a standard Ficoll-Paque TM density gradient method to establish a control value. The density gradient method was performed as described in a brochure prepared by Pharmacia Fine Chemicals entitled Ficoll-Paque TM *For In Vitro Isolation of Lymphocytes*. The blood was treated by an anticoagulation agent, EDTA, prior to use in any of the examples.

The yield obtained using the Ficoll-Paque TM method was 90% of the mononuclear cells present in the blood sample. The absolute value of the mononuclear cells present in the blood sample was determined by standard microscopic stain analysis. The granulocyte level present in the mononuclear cells was 0.4%.

EXAMPLE 1

An aliquot of the blood sample was placed on top of a polyester, thixotropic gel having a density of 1.077 grams/ml. Centrifugation was effected at $900 \times G$ for 10 minutes. The cells were harvested after syphoning off the plasma by adding buffered saline and providing gentle turbulene to the cells with a bulb and pipette. The yield of mononuclear cells was 84% and the granulocyte level in the mononuclear cells was 10.28%.

EXAMPLE 2

The method of Example 1 was repeated using an aliquot of the blood sample which was diluted with an equal volume of buffered, isotonic salt solution (2 ml blood sample + 2 ml buffered salt solution). The yield of mononuclear cells was 64% of the theoretical yield and the granulocyte content was 3.25%.

EXAMPLE 3

The method of the present invention was used to isolate the mononuclear cells in an aliquot of the blood sample. 1.2 grams of a thixotropic, polyester gel having a density of 1.077 grams/ml was placed in a 7 ml test tube. 1.0 grams of a density gradient material containing 5.8 grams of sucrose polymer and 10 grams of diatrizoate sodium dissolved in water was placed in the test tube. The test tube was subjected to pre-centrifugation so as to form a barrier layer of the gel material above the density gradient material. An aliquot of the blood sample was placed on top of the gel barrier layer. Centrifugation was effected at $900 \times G$ for 10 minutes. The cells were harvested after syphoning off the plasma by adding buffered saline and providing gentle turbulence to the cells with a bulb and pipette. The yield of mononuclear cells was 80% and the granulocyte content was 1.65%.

EXAMPLE 4

The procedure of Example 3 was repeated with the exception that the aliquot of the blood sample was diluted with an equal volume of buffered, isotonic salt solution. The yield of mononuclear cells was 60% and the granulocyte content was 1.94%.

EXAMPLE 5

The procedure of Example 3 was used in comparison with the Ficoll-Paque density gradient method on blood samples extracted from 5 separate subjects. Table 1, hereinbelow, illustrates the average yield and times required to perform the analysis:

TABLE I

| Results | Procedure of Example 3 | Ficoll-Paque TM Method |
|---|---|---|
| Yield of mononuclear cells | 36.4% | 36.5% |
| Granulocytes | 1.88% | 1.10% |

TABLE I-continued

| Results | Procedure of Example 3 | Ficoll-Paque ™ Method |
| --- | --- | --- |
| Dilution step, minutes | 0 min | 0 min |
| Tube Preparation, minutes | 0 min | 3 min |
| Layering of blood, minutes | 3 min | 3 min |
| Centrifugation | 15 min | 40 min |

What is claimed is:

1. A blood separation device suitable for the separation and partition of mononuclear cells from a blood sample, which comprises:
   a centrifuge tube having a bottom closed end and an opposite top open end;
   a water soluble density gradient material disposed adjacent to the bottom closed end of the tube prior to centrifugation of the blood separation device; and
   a thixotropic gel-like substance disposed adjacent to and on top of the water soluble density gradient material prior to centrifugation of the blood separation device, the thixotropic gel-like substance acting as a partition between the water soluble density gradient material and a blood sample placed in the tube on top of the gel and acting to keep the water soluble density gradient material in place in the bottom of the tube and separated from the blood sample prior to centrifugation, the thixotropic gel being substantially hydrophobic, the water soluble density gradient material having a specific gravity which is higher than that of the thixotropic gel-like substance.

2. A centrifuge tube in accordance with claim 1 wherein said gel-like substance is a polyester.

3. A centrifuge tube in accordance with claim 1 wherein said gel-like substance is a mixture of silicone fluid and a hydrophobic powdered silica.

4. A centrifuge tube in accordance with claim 1 wherein said gel-like substance is a mixture of a hydrocarbon polymer and a powdered silica.

5. A centrifuge tube in accordance with claim 1 wherein said thixotropic, gel-like substance has a specific gravity of from about 1.07 to about 1.085 g/cc.

6. A centrifuge tube in accordance with claim 1 wherein said thixotropic, gel-like substance has a specific gravity of from about 1.075 to about 1.08 g/cc.

7. A centrifuge tube in accordance with claim 1 wherein said density gradient material has a specific gravity of from about 1.080 to about 1.100 g/cc.

8. A centrifuge tube in accordance with claim 1 wherein density gradient material has a specific gravity of from about 1.085 to about 1.095 g/cc.

9. A centrifuge tube in accordance with claim 1 wherein said thixotropic, gel-like material has a specific gravity of 1.077 g/cc and said density gradient material has a specific gravity of 1.09 g/cc.

10. A centrifuge tube suitable for the separation and partition of mononuclear cells from a blood sample comprising a centrifuge tube having located therein a thixotropic, gel-like substance and a water soluble density gradient material having a specific gravity higher than that of said gel-like substance, said density gradient material being an aqueous solution of a polymeric saccharide and diatrizoate.

11. A centrifuge tube suitable for the separation and partition of mononuclear cells from a blood sample comprising a centrifuge tube having located therein a thixotropic, gel-like substance selected from the group consisting of a polyester, a mixture of silicone fluid and a hydrophobic powdered silica, and a mixture of a hydrocarbon polymer and a powdered silica, and a water soluble density gradient material having a specific gravity higher than that of said gel-like substance, wherein said water soluble density gradient material comprises an aqueous solution of a polymeric saccharide and diatrizoate.

12. A centrifuge tube in accordance with claim 11 wherein said thioxotropic, gel-like substance has a specific gravity of from about 1.07 to about 1.085 g/cc.

13. A centrifuge tube in accordance with claim 11 wherein said water-soluble density gradient material has a specific gravity of from about 1.080 to about 1.100 g/cc.

14. A centrifuge tube in accordance with claim 11 wherein said thixotropic, gel-like substance has a specific gravity of from about 1.075 to about 1.08 g/cc.

15. A centrifuge tube in accordance with claim 11 wherein said density gradient material has a specific gravity of from about 1.085 to about 1.095 g/cc.

16. A centrifuge tube in accordance with claim 11 wherein said thixotropic, gel-like material has a specific gravity of 1.077 g/cc and said density gradient material has a specific gravity of 1.09 g/cc.

* * * * *